United States Patent [19]
Katsumata et al.

[11] Patent Number: 5,439,822
[45] Date of Patent: Aug. 8, 1995

[54] GENE EXPRESSION REGULATORY DNA

[75] Inventors: Ryoichi Katsumata; Yutaka Takano, both of Tokyo, Japan

[73] Assignee: Kyowa Hakko Kogyo Co., Ltd., Tokyo, Japan

[21] Appl. No.: 938,333

[22] Filed: Aug. 28, 1992

[30] Foreign Application Priority Data

Sep. 2, 1991 [JP] Japan ................................. 3-221885

[51] Int. Cl.$^6$ ........................ C12N 1/21; C12N 15/11; C12N 15/60; C12N 15/77
[52] U.S. Cl. ............................ 435/252.32; 435/69.1; 435/172.3; 435/195; 435/320.1; 536/24.1
[58] Field of Search .................. 435/69.1, 71.2, 172.3, 435/252.32, 320.1, 195, 252.32; 935/29, 48, 72; 536/24.1

[56] References Cited

U.S. PATENT DOCUMENTS 4,965,197  10/1990  Liebl ................. 435/172.3

FOREIGN PATENT DOCUMENTS

| | | |
|---|---|---|
| 0178744 | 4/1986 | European Pat. Off. |
| 0215388 | 3/1987 | European Pat. Off. |
| 0271838 | 6/1988 | European Pat. Off. |
| 2590592 | 11/1986 | France . |
| 259637 | 8/1988 | Germany . |
| 61-124387 | 6/1986 | Japan . |

OTHER PUBLICATIONS

Matsuoka, et al. "Isolation, Hyperexpression, and sequencing of the aceA Gene Encoding Isocitrate Lyase in *Escherichia coli*", J. of Bacteriology 170: 4528–4536, 1988.
Chung et al. "Glyoxylate Bypass Operon of *Escherichia coli*: Cloning and Determination of the Functional Map", J. Bacteriol. 170: 3861988.
Cadenas et al., Gene 98:117–121 (1991).
Eikmanns et al., Gene 102:93–98 (1991).
Tsuchiya et al., Bio/Technology 6:428–430 (1988).

*Primary Examiner*—Richard A. Schwartz
*Assistant Examiner*—Nancy J. Vogel
*Attorney, Agent, or Firm*—White & Case

[57] ABSTRACT

The present invention provides a gene expression regulatory DNA and a process for preparing a protein using the same.

A DNA derived from the isocitrate lyase (ICL) gene of a coryneform bacterium regulates expression of a structural gene encoding a protein when incorporated into a vector DNA together with said structural gene and introduced into a host coryneform bacterium, and a useful protein can be efficiently produced using the DNA.

8 Claims, 6 Drawing Sheets

Ba.BamHI.Bg.BglII,E.EcoRI,H.HindIII,Hp.HpaI,K.KpnI,S.SalI,
Sa.SacI,Sm.SmaI,Sp.SphI,P.PstI,Xb.XbaI ■ CHROMOSOMAL DNA FRAGMENT FROM CORYNEBACTERIUM
GLUTAMICUM ATCC 13032
(6.0 kb HindIII-FRAGMENT)

FIG. 5
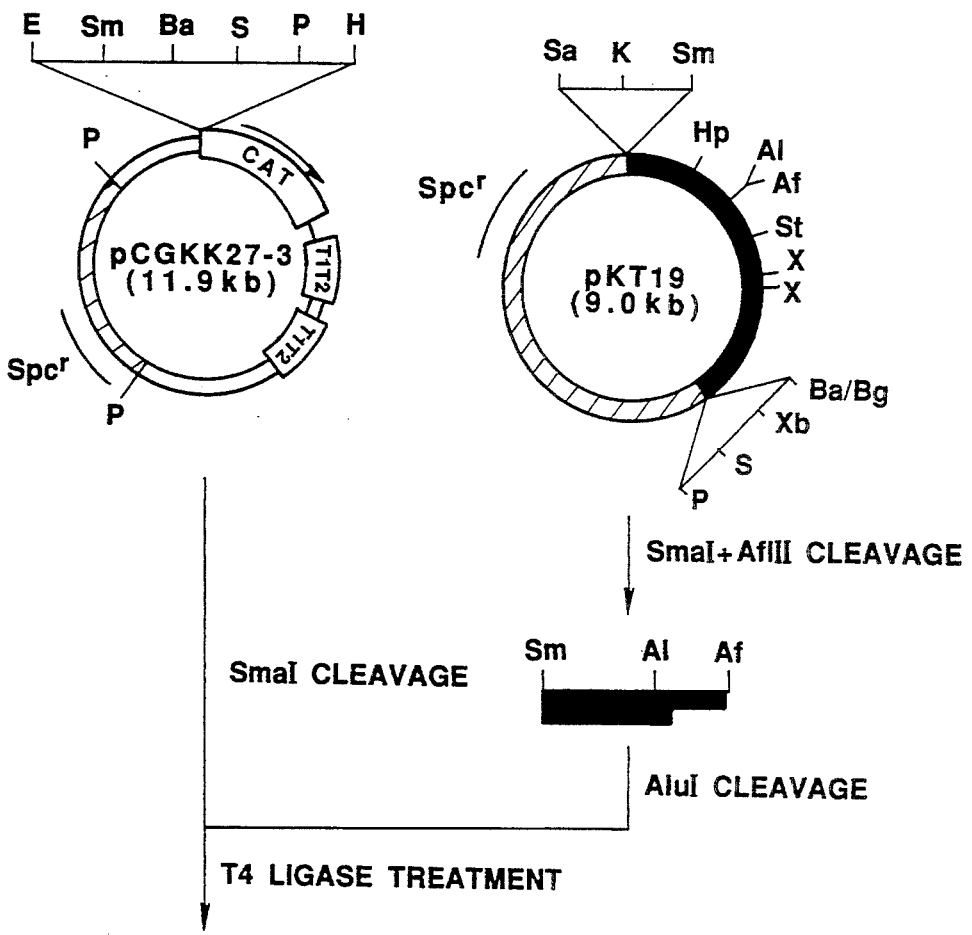
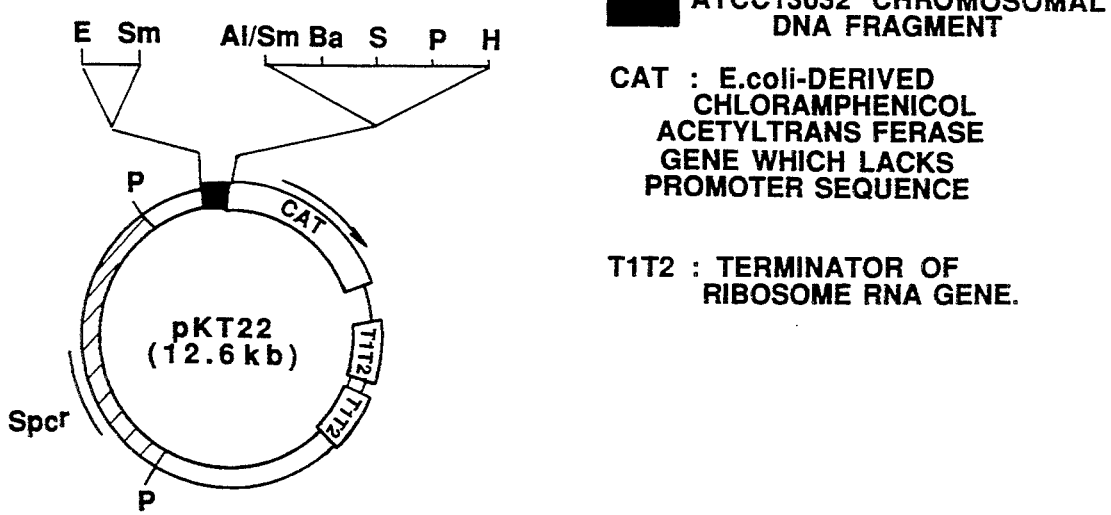

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH:18 amino acid
        ( B ) TYPE:amino acid
        ( C ) STRANDEDNESS:single
        ( D ) TOPOLOGY:linear ( i i ) MOLECULE TYPE:peptide ( v ) FRAGMENT TYPE:N-terminal fragment ( x i ) SEQUENCE DESCRIPTION: SEQ ID NO:1:

Ser Asn Val Gly Lys Pro Arg Thr Ala Gln Glu Ile Gln Gln Asp Asp
1              5                      10                 15

Asp Thr ( 2 ) INFORMATION FOR SEQ ID NO:2:

( i ) SEQUENCE CHARACTERISTICS:
        ( A ) LENGTH:50 base pairs
        ( B ) TYPE:nucleic acid
        ( C ) STRANDEDNESS:single
        ( D ) TOPOLOGY:linear ( i i ) MOLECULE TYPE:Other nucleic acid Synthetic DNA ( i i i ) HYPOTHETICAL:YES ( i v ) ANTI-SENSE:YES ( v ) FRAGMENT TYPE:N-terminal fragment ( x i ) SEQUENCE DESCRIPTION: SEQ ID NO:2:

GTATCATCAT CCTGCTGGAT TTCCTGGGCG GTGCGTGGCT TGCCAACGTT    50

( 2 ) INFORMATION FOR SEQ ID NO:3:

( i ) SEQUENCE CHARACTERISTICS:
        ( A ) LENGTH:2135 base pairs
        ( B ) TYPE:nucleic acid
        ( C ) STRANDEDNESS:double
        ( D ) TOPOLOGY:linear ( i i ) MOLECULE TYPE:Genomic DNA ( v i ) ORIGINAL SOURCE:
        ( A ) ORGANISM:Corynebacterium glutamicum
        ( B ) STRAIN:ATCC13032

( i x ) FEATURE:
        ( A ) NAME/KEY:mat peptide
        ( B ) LOCATION:514 to 1806
        ( C ) IDENTIFICATION METHOD:E ( x i ) SEQUENCE DESCRIPTION: SEQ ID NO:3:

```
GTTAACGGTT GTGAAAACTC TTTTAAGAAA AGCACTCTGA CTACCTCTGG AATCTAGGTG      60

CCACTCTTCT TTCGATTTCA ACCCTTATCG TGTTTGGCGA TGTGATCAGA CTAAGTGATC     120

ACCGTCACCA GCAAAGGGG TTTGCGAACT TTACTAAGTC ATTACCCCCG CCTAACCCCG      180

ACTTTTATCT AGGTCACACC TTCGAAACCT ACGGAACGTT GCGGTGCCTG CATTTTCCA      240

TTTCAGAGCA TTTGCCCAGT ACATCCGTAC TAGCAACTCC CCCGCCCACT TTTCTGCGA      300

AGCCAGAACT TTGCAAACTT CACAACAGGG GTGACCACCC GCACAAAACT TAAAAACCCA     360

AACCGATTGA CGCACCAATG CCCGATGGAG CAATGTGTGA ACCACGCCAC CACGCAAACC     420

GATGCACATT ACGTCGAAAC AGTGACAGTG CATTAGCTCA TACTTTGTGG TGGCACCGCC     480

CATTGCGAAT CAGCACTTAA GGAAGTGACT TTG ATG TCA AAC GTT GGA AAG CCA     534
                                     Met Ser Asn Val Gly Lys Pro
                                      1               5

CGT ACC GCA CAG GAA ATC CAG CAG GAT TGG GAC ACC AAC CCT CGT TGG     582
Arg Thr Ala Gln Glu Ile Gln Gln Asp Trp Asp Thr Asn Pro Arg Trp
        10                  15                  20

AAC GGC ATC ACC CGC GAC TAC ACC GCA GAC CAG GTA GCT GAT CTG CAG     630
Asn Gly Ile Thr Arg Asp Tyr Thr Ala Asp Gln Val Ala Asp Leu Gln
        25                  30                  35

GGT TCC GTC ATC GAG GAG CAC ACT CTT GCT GCC GCG GCT CAG AGA TCC     678
Gly Ser Val Ile Glu Glu His Thr Leu Ala Ala Ala Ala Gln Arg Ser
40                  45                  50                  55

TCT GGG ACG CAG TCA CCC AGG AAG GTG ACG GAT ACA TCA ACG CTT GGC     726
Ser Gly Thr Gln Ser Pro Arg Lys Val Thr Asp Thr Ser Thr Leu Gly
        60                  65                  70

GCA CTC ACC GGT AAC CAG GCT GTT CAG CAG GTT CGT GCA GGC CTG AAG     774
Ala Leu Thr Gly Asn Gln Ala Val Gln Gln Val Arg Ala Gly Leu Lys
        75                  80                  85

GCT GTC TAC CTG TCC GGT TGG CAG GTC GCA GGT GAC GCC AAC CTC TCC     822
Ala Val Tyr Leu Ser Gly Trp Gln Val Ala Gly Asp Ala Asn Leu Ser
        90                  95                 100

GGC CAC ACC TAC CCT GAC CAG TCC CTC TAC CCA GCG AAC TCC GTT CCA     870
Gly His Thr Tyr Pro Asp Gln Ser Leu Tyr Pro Ala Asn Ser Val Pro
105                 110                 115

AGC GTC GTT CGT CGC ATC AAC AAC GCA CTG CTG CGT TCC GAT GAA ATC     918
Ser Val Val Arg Arg Ile Asn Asn Ala Leu Leu Arg Ser Asp Glu Ile
120                 125                 130                 135

GCA CGC ACC GAA GCG ACA CCT CCG TTG ACA ACT GGG TTG TCC CAA TCG     966
Ala Arg Thr Glu Ala Thr Pro Pro Leu Thr Thr Gly Leu Ser Gln Ser
        140                 145                 150

TCG CGG ACG GCG AAG TGG CTT CGG TGG AGC ACT CAA CGT CTA CAA CTC    1014
Ser Arg Thr Ala Lys Trp Leu Arg Trp Ser Thr Gln Arg Leu Gln Leu
```

|   |   |   |   |   |   |   |   |   |   |   |   |   |   |   |   |      |
|---|---|---|---|---|---|---|---|---|---|---|---|---|---|---|---|------|
|   |   |   | 155 |   |   |   |   |   | 160 |   |   |   |   |   | 165 |   |

```
CAG  AAG  GCA  ATG  ATC  GCA  GCT  GGC  GCT  GCA  GGC  ACC  CAC  TGG  GAA  GAC        1062
Gln  Lys  Ala  Met  Ile  Ala  Ala  Gly  Ala  Ala  Gly  Thr  His  Trp  Glu  Asp
          170                      175                     180

CAC  GTC  GCT  TCT  GAA  AAG  AAG  TGT  GGC  CAC  CTC  GGC  GGC  AAG  GTT  CTG        1110
His  Val  Ala  Ser  Glu  Lys  Lys  Cys  Gly  His  Leu  Gly  Gly  Lys  Val  Leu
185                      190                     195

ATC  CCA  ACC  CAG  CAG  CAC  ATC  CGC  ACC  CTG  AAC  TCT  GCC  CGC  CTT  GCA        1158
Ile  Pro  Thr  Gln  Gln  His  Ile  Arg  Thr  Leu  Asn  Ser  Ala  Arg  Leu  Ala
200                      205                     210                         215

GCA  GAC  GTT  GCA  AAC  ACC  CCA  ACT  GTT  GTT  ATC  GCA  CGT  ACC  GAC  GCT        1206
Ala  Asp  Val  Ala  Asn  Thr  Pro  Thr  Val  Val  Ile  Ala  Arg  Thr  Asp  Ala
                    220                     225                     230

GAG  GCA  GCA  ACC  CTG  ATC  ACC  TCT  GAC  GTT  GAT  GAG  CGC  GAC  CAA  CCA        1254
Glu  Ala  Ala  Thr  Leu  Ile  Thr  Ser  Asp  Val  Asp  Glu  Arg  Asp  Gln  Pro
               235                     240                     245

TTC  ATC  ACC  GGT  GAG  CGC  ACC  GCA  GAA  GGC  TAC  TAC  CAC  GTC  AAG  AAT        1302
Phe  Ile  Thr  Gly  Glu  Arg  Thr  Ala  Glu  Gly  Tyr  Tyr  His  Val  Lys  Asn
          250                     255                     260

GGT  CTC  GAG  CCA  TGT  ATC  GCA  CGT  GCA  AAG  TCC  TAC  GCA  CCA  TAC  GCA        1350
Gly  Leu  Glu  Pro  Cys  Ile  Ala  Arg  Ala  Lys  Ser  Tyr  Ala  Pro  Tyr  Ala
265                     270                     275

GAT  ATG  ATC  TGG  ATG  GAG  ACC  GGC  ACC  CCT  GAC  CTG  GAG  CTC  GCT  AAG        1398
Asp  Met  Ile  Trp  Met  Glu  Thr  Gly  Thr  Pro  Asp  Leu  Glu  Leu  Ala  Lys
280                     285                     290                         295

AAG  TTC  GCT  GAA  GGC  GTT  CGC  TCT  GAG  TTC  CCA  GAC  CAG  CTG  CTG  TCC        1446
Lys  Phe  Ala  Glu  Gly  Val  Arg  Ser  Glu  Phe  Pro  Asp  Gln  Leu  Leu  Ser
                         300                     305                     310

TAC  AAC  TGC  TCC  CCA  TCC  TTC  AAC  TGG  TCT  GCA  CAC  CTC  GAG  GCA  GAT        1494
Tyr  Asn  Cys  Ser  Pro  Ser  Phe  Asn  Trp  Ser  Ala  His  Leu  Glu  Ala  Asp
               315                     320                     325

GAG  ATC  GCT  AAG  TTC  CAG  AAG  GAA  CTC  GGC  GCA  ATG  GGC  TTC  AAG  TTC        1542
Glu  Ile  Ala  Lys  Phe  Gln  Lys  Glu  Leu  Gly  Ala  Met  Gly  Phe  Lys  Phe
          330                     335                     340

CAG  TTC  ATC  ACC  CTC  GCA  GGC  TTC  CAC  TCC  CTC  AAC  TAC  GGC  ATG  TTC        1590
Gln  Phe  Ile  Thr  Leu  Ala  Gly  Phe  His  Ser  Leu  Asn  Tyr  Gly  Met  Phe
345                     350                     355

GAC  CTG  GCT  TAC  GGA  TAC  GCT  CGC  GAA  GGC  ATG  ACC  TCC  TTC  GTT  GAC        1638
Asp  Leu  Ala  Tyr  Gly  Tyr  Ala  Arg  Glu  Gly  Met  Thr  Ser  Phe  Val  Asp
360                     365                     370                         375

CTG  CAG  AAC  CGT  GAG  TTC  AAG  GCA  GCT  GAA  GAG  CGT  GGC  TTC  ACC  GCT        1686
Leu  Gln  Asn  Arg  Glu  Phe  Lys  Ala  Ala  Glu  Glu  Arg  Gly  Phe  Thr  Ala
                    380                     385                     390

GTT  AAG  CAC  CAG  CGT  GAG  GTT  GGC  GCA  GGC  TAC  TTC  GAC  CAG  ATC  GCA        1734
Val  Lys  His  Gln  Arg  Glu  Val  Gly  Ala  Gly  Tyr  Phe  Asp  Gln  Ile  Ala
               395                     400                     405

ACC  ACC  GTT  GAC  CCG  AAC  TCT  TCT  ACC  ACC  GCT  TTG  AAG  GGT  TCC  ACT        1782
Thr  Thr  Val  Asp  Pro  Asn  Ser  Ser  Thr  Thr  Ala  Leu  Lys  Gly  Ser  Thr
          410                     415                     420

GAA  GAA  GGC  CAG  TTC  CAC  AAC  TAG  GACCTACAGG  TTCTGACAAT  TTAAATCTCC            1836
Glu  Glu  Gly  Gln  Phe  His  Asn  Xaa
425                     430

CTACATCTGT  ACAACGGATG  TAGGGAGTTT  TTCCTTATAT  ATGCCCTCCA  CAAATCCCCT             1896

ATCGTGTGAG  ATGTGTTTCA  TAGGTGCCCC  CAACGTTGCC  TGTTGACTGC  AAATTTTCCG             1956

AAAGAATCCA  TAAACTACTT  CTTTAAGTCG  CCAGATTAAA  GTCGTCAATG  AAAGGACATA             2016

CATGTCTATT  TCCCGCACCG  TCTTCGGCAT  CGCAGCCACC  GCAGCCCTGT  CTGCAGCTCT             2076

CGTTGCGTGT  TCTCCACCTC  ACCAGCAGGA  TTCCCCAGTC  CAGCGCACCA  ATGAGATCT              2135
```

( 2 ) INFORMATION FOR SEQ ID NO:4:

(i) SEQUENCE CHARACTERISTICS:
    (A) LENGTH:702 base pairs
    (B) TYPE:nucleic acid
    (C) STRANDEDNESS:double
    (D) TOPOLOGY:linear (ii) MOLECULE TYPE:Genomic DNA (v) FRAGMENT TYPE:N-terminal fragment (vi) ORIGINAL SOURCE:
    (A) ORGANISM:Corynebacterium glutamicum
    (B) STRAIN:ATCC13032

(ix) FEATURE:
    (A) NAME/KEY:transit peptide
    (B) LOCATION:514 to 702
    (C) IDENTIFICATION METHOD:E (xi) SEQUENCE DESCRIPTION: SEQ ID NO:4:

```
GTTAACGGTT GTGAAAACTC TTTTAAGAAA AGCACTCTGA CTACCTCTGG AATCTAGGTG    60

CCACTCTTCT TTCGATTTCA ACCCTTATCG TGTTTGGCGA TGTGATCAGA CTAAGTGATC   120

ACCGTCACCA GCAAAGGGG  TTTGCGAACT TTACTAAGTC ATTACCCCCG CCTAACCCCG   180

ACTTTTATCT AGGTCACACC TTCGAAACCT ACGGAACGTT GCGGTGCCTG CATTTTCCA    240

TTTCAGAGCA TTTGCCCAGT ACATCCGTAC TAGCAACTCC CCCGCCCACT TTTTCTGCGA   300

AGCCAGAACT TTGCAAACTT CACAACAGGG GTGACCACCC GCACAAAACT TAAAAACCCA   360

AACCGATTGA CGCACCAATG CCCGATGGAG CAATGTGTGA ACCACGCCAC CACGCAAACC   420

GATGCACATT ACGTCGAAAC AGTGACAGTG CATTAGCTCA TACTTTGTGG TGGCACCGCC   480

CATTGCGAAT CAGCACTTAA GGAAGTGACT TTG ATG TCA AAC GTT GGA AAG CCA   534
                                    Met Ser Asn Val Gly Lys Pro
                                     1               5

CGT ACC GCA CAG GAA ATC CAG CAG GAT TGG GAC ACC AAC CCT CGT TGG    582
Arg Thr Ala Gln Glu Ile Gln Gln Asp Trp Asp Thr Asn Pro Arg Trp
        10              15                      20

AAC GGC ATC ACC CGC GAC TAC ACC GCA GAC CAG GTA GCT GAT CTG CAG    630
Asn Gly Ile Thr Arg Asp Tyr Thr Ala Asp Gln Val Ala Asp Leu Gln
    25              30                  35

GGT TCC GTC ATC GAG GAG CAC ACT CTT GCT GCC GCG GCT CAG AGA TCC    678
Gly Ser Val Ile Glu Glu His Thr Leu Ala Ala Ala Ala Gln Arg Ser
40                  45                  50                  55

TCT GGG ACG CAG TCA CCC AGG AAG                                    702
Ser Gly Thr Gln Ser Pro Arg Lys
            60
```

GENE EXPRESSION REGULATORY DNA

BACKGROUND OF THE INVENTION

The present invention relates to a novel DNA which is obtained from a coryneform bacterium and which regulates expression of a structural gene and to a process for efficiently producing a useful protein using the DNA. "Coryneform bacteria" hereinafter refers to microorganisms belonging to the genus Corynebacterium, Brevibacterium or Microbacterium.

Development of recombinant DNA technology has enabled utilization of various microorganisms for the production of useful polypeptides which are products of heterologous organisms. However, when a genetic product of a foreign gene is toxic to a host, expression of the foreign gene from the beginning of growth of the host causes death or growth inhibition of the host. Therefore, it is difficult to produce the genetic product in large quantities. To overcome such problem, it has been necessary to employ an expression system for inducing the expression of the foreign gene after the growth phase of a host microorganism. In *E. coli* which is most frequently used as a host, the expression systems for genes utilizing promoters working in response to a specific compound or under specific physical conditions have been established [Goeddel, D., et al., Proc. Natl. Acad. Sci. U.S.A., 76, 106 (1979), Edman, J. C., et al., Nature, 291, 503 (1981), Shimatake, H., et al., Nature, 292, 128 (1981)]. By use of these systems, a variety of useful proteins have been produced.

On the other hand, recombinant DNA technology is also applicable to coryneform bacteria which are used for production of various amino acids, purine nucleotides, and the like by fermentation. For example, a promoter for coryneform bacteria for structurally expressing a reporter gene has been obtained using a vector for detecting a promoter functioning in such bacteria (EP-A-271838). However, there are no reports of the successful development of a promoter for regulating expression in coryneform bacteria. On the other hand, a method for artificially regulating expression of a foreign gene in a coryneform bacterium using the aforesaid promoter for *E. coli* capable of inducing expression of a foreign gene in *E. coli* to induce the expression of the chloramphenicol acetyltransferase gene in coryneform bacterium has been reported (EP-B-215388). However, this method for expression is not sufficiently potent and the yield of the genetic product accumulated is small as compared with the yield obtained by using *E. coli* as the host.

Accordingly, in order to efficiently produce useful genetic products in coryneform bacteria, it is necessary to develop a DNA which functions in such host bacteria and which enables artificial regulation of expression of a structural gene.

SUMMARY OF THE INVENTION

The present invention provides a DNA and method by which expression is regulated in coryneform bacteria in response to environmental conditions such as the composition of the medium. More specifically, it has been found that the expression of isocitrate lyase (hereinafter referred to as ICL) gene of such bacteria is repressed when the carbon sources in a medium are sugars such as glucose, sucrose and maltose. When the carbon sources in the medium are non-sugars such as acetic acid, lactic acid and ethanol, or in the absence of sugars, expression is induced and the level of the expression is extremely high. A DNA fragment encoding the ICL gene has been cloned and the nucleotide sequence of a DNA which regulates the expression of the gene has been determined. It has thus been found that the DNA is novel and a desired gene can be efficiently expressed in coryneform bacteria, using this DNA.

In the amino acid fermentation by coryneform bacteria by known processes, the culture containing microbial cells is usually discarded after sugars in the medium is consumed and fermentation is completed. Introduction of the DNA of the present invention into a coryneform bacterium enables use of the culture for producing a protein under the conditions where no sugars are present. Therefore, by the present invention, the culture of a coryneform bacterium used for amino acid fermentation can be reutilized for the production of a protein.

BRIEF DESCRIPTION OF THE DRAWINGS

FIG. 5 shows the steps for preparing pKT22.

DETAILED DESCRIPTION OF THE INVENTION

Figure 1:
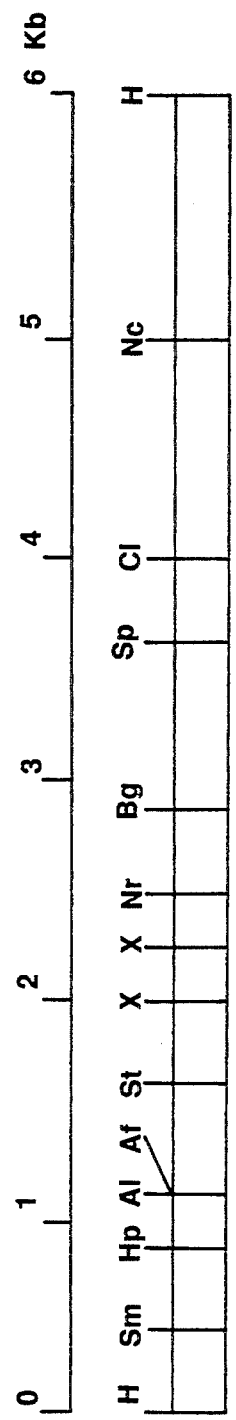
FIG. 1 is a restriction map of a cloned Hind III-cleaved DNA fragment of 6.0 kb carrying the ICL gene.

According to the present invention, a DNA derived from the ICL gene of a coryneform bacterium is incorporated into a vector DNA together with a structural gene encoding a protein and then introduced into a coryneform host microorganism. The DNA (hereinafter referred to as ICL promoter) regulates the expression of the structural gene in the host. More particularly, the expression of the structural gene is repressed when carbon sources in the medium are sugars, and the expression is induced when carbon sources in the medium are non-sugars or no sugars are present in the medium.

A DNA carrying the ICL promoter and ICL structural gene may be isolated from any coryneform bacteria, but the following strains are preferably used.

Corynebacterium glutamicum ATCC 13032
Corynebacterium acetoacidophilum ATCC 13870
Corynebacterium acetoglutamicum ATCC 15806
Corynebacterium callunae ATCC 15991
Corynebacterium herculis ATCC 13868
Corynebacterium melassecola ATCC 17965
Corynebacterium lilium ATCC 15990
Brevibacterium immariophilum ATCC 14068
Brevibacterium saccharolyticum ATCC 14066
Brevibacterium thiogenitalis ATCC 19240
Brevibacterium divaricatum ATCC 14020
Brevibacterium flavum ATCC 14067
Brevibacterium lactofermentum ATCC 13869
Brevibacterium roseum ATCC 13825
Microbacterium ammoniaphilum ATCC 15354

Extraction of a chromosomal DNA from coryneform bacteria is carried out by known procedure, for example, the method described in Japanese Published Unexamined Patent Application No. 126789/83. The DNA fragment containing the ICL gene region can be isolated from this chromosomal DNA by incorporating the chromosomal DNA treated with an appropriate restriction enzyme into a plasmid or a phage DNA treated with the same restriction enzyme or a restriction enzyme which causes the same cohesive end, transforming a microorganism with the resultant recombinant DNA, and then isolating a clone carrying the recombinant DNA containing the desired DNA fragment.

For example, when E. coli is used as a host for transformation and a plasmid is used as a vector, the clone carrying the DNA fragment containing the ICL gene on the plasmid vector can be isolated by detecting a transformant carrying the DNA fragment which hybridizes to a synthetic DNA encoding a part of the amino acid sequence of ICL using colony hybridization [Hanahan, D. et al., Gene, 10, 63 (1980)]. The synthetic DNA used as a probe may be obtained, for example, by isolating ICL, determining the amino acid sequence at the N-terminus thereof, and chemically synthesizing a polynucleotide corresponding to the sequence in a conventional manner [M. H. Caruther et al., Chemical Synthesis of Gene Fragments, a Laboratory Manual, Verlag, Chemie (1982)]. A series of fundamental operations required for the cloning in E. coli are known and described in detail in Molecular Cloning (1982), Cold Spring Harbor Laboratory.

By introducing the cloned fragment obtained by the above method into coryneform bacteria, it can be confirmed that the cloned fragment carries the ICL promoter and the structural gene encoding ICL. For this purpose, the E. coli plasmid carrying the cloned fragment is ligated to a vector capable of autonomous replication in coryneform bacteria, or the cloned fragment is inserted in a vector for coryneform bacteria, to prepare a recombinant plasmid. Such recombinant DNA can be prepared by in vitro recombination, followed by transformation of a coryneform bacteria strain and selection of a transformant carrying a plasmid having the desired structure. Any vector may be used as the vector for coryneform bacteria so long as it is capable of autonomous replication in such bacteria. Examples of suitable vectors are pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pAM330 (Japanese Published Unexamined Patent Application No. 67699/83), pAG1, pAG3, pAG14, pAG50 (Japanese Published Unexamined Patent Application No. 166890/87) and plasmids derived therefrom. In order to prepare plasmids from coryneform bacteria, a known method, for example, the method described in Japanese Published Unexamined Patent Application No. 134500/82 may be used. Transformation of coryneform bacteria is carried out by a method using protoplasts (e.g., Japanese Published Unexamined Patent Application No. 186492/82) or electroporation [Appl. Microbiol. Biotechnol., 30, 283 (1989)].

The thus prepared recombinant DNA is used to transform an ICL activity-deficient mutant coryneform bacteria strain. If the transformants obtained have acquired the ability of ICL synthesis, it indicates that the ICL gene is present on the cloned fragment. Alternatively, a wild strain having ICL activity may be transformed with the recombinant plasmid. In such case, the presence of the ICL gene can be confirmed by an increase in ICL activity as compared with the host when cultured in a medium containing non-sugars such as acetic acid, lactic acid and ethanol as carbon sources, or in a medium where no sugar is present. From positive transformants, plasmids are extracted. By digestion of the plasmids with restriction enzymes followed by agarose gel electrophoresis, a DNA fragment containing the inserted ICL gene can be isolated.

The ICL gene-carrying DNA fragment is subcloned and deletion plasmids including various degraded small fragments are examined for ICL activity-conferring ability or ICL activity-enhancing ability, whereby the presence of ICL gene can be further specified. The nucleotide sequence of the DNA fragment carrying the ICL gene can be determined by the dideoxynucleotide synthesis chain termination method [J. Mol. Biol., 94, 441 (1975)], the Maxam-Gilbert method [Proc. Natl. Acad. Sci., 74, 560 (1977)], or by similar known methods. An open reading frame can be presumed by finding the nucleotide sequence encoding the N-terminal amino acid sequence of ICL on the DNA nucleotide sequence. Based on the presence of the open reading frame, it is assumed that the region having the ICL promoter activity is present upstream of the open reading frame.

By such analysis, in the case of, for example, *Corynebacterium glutamicum* ATCC 13032 described in the examples, the ICL promoter activity of the strain can be specified to be attributed to the sequence at positions 1 through 513 on the DNA nucleotide sequence shown by Seq. ID NO:3. The ICL promoter activity of the present invention is not limited to this DNA sequence. The DNA sequence may be partly deleted or modified as long as the promoter activity is not damaged.

An expression vector can be obtained by inserting a DNA which contains the DNA fragment having the ICL promoter activity, and downstream from the fragment, a structural gene and the terminator for terminating transcription into the above-mentioned plasmid capable of autonomous replication in coryneform bacteria. As the terminator, it is preferred to use the terminator of the ICL gene, but terminators from other genes of coryneform bacteria or ρ-independent terminator derived from *E. coli* or *B. subtilis* genes [Ann. Rev. Genet., 13, 319 (1979)] may also be used. Examples of appropriate structural genes are those of enzymes such as β-galactosidase, chloramphenicol acetyltransferase and ICL, and physiologically active proteins such as insulin, growth hormone, α-, β- or γ-interferon and granulocyte colony stimulating factor (G-CSF).

A host is transformed with the expression vector described above and the transformants are cultured to express the desired genetic product. As the host, it is preferred to use the aforesaid coryneform bacteria, but other coryneform bacteria may also be used.

By culturing the transformants in a medium containing, as carbon sources, non-sugars such as acetic acid and lactic acid, and further containing nitrogen sources, inorganic materials, vitamins, etc., the desired genetic products are accumulated in the medium. Alternatively, the transformants are initially grown in a medium containing, as carbon sources, sugars such as glucose, sucrose and maltose, and after the sugars are consumed, the non-sugar carbon sources described above are added to the medium or the medium is replaced with the one containing no sugar, followed by further culturing to obtain the desired genetic products.

Culturing is carried out under aerobic conditions with aeration or stirring. In general, it is preferred to keep the pH of the medium around neutrality during the culturing. Conditions such as culturing temperature and time are adjusted to provide maximum proliferation of the host microorganism and the maximum production of the genetic products by the transformants. Generally, it is suitable to carry out culturing at a temperature of 15° to 40° C. for 4 to 72 hours.

The genetic products accumulated in the culture are extracted by disrupting the microbial cells in conventional manner, for example, by mechanical disruption or by a method using a bacteriolytic enzyme. Isolation and purification of the desired genetic products from the extract can be carried out by combinations of methods conventionally used for the purification of proteins, for example, precipitation using a precipitating agent, dialysis, electrophoresis, chromatography using ion exchange resin or the like, gel filtration and a method using an antibody column.

Certain embodiments of the present invention are illustrated in the following representative examples.

EXAMPLE 1

Mode of Expression of ICL Gene of Coryneform bacteria

In this example, the following coryneform bacteria were used: *Corynebacterium glutamicum* ATCC 13032, *Corynebacterium acetoacidophilum* ATCC 13870, *Corynebacterium callunae* ATCC 15991, *Corynebacterium herculis* ATCC 13868, *Corynebacterium lilium* ATCC 15990, *Brevibacterium immariophilum* ATCC 14068, *Brevibacterium divaricatum* ATCC 14020, *Brevibacterium flavum* ATCC 14067, *Brevibacterium lactofermentum* ATCC 13655 and *Microbacterium ammoniaphilum* ATCC 15354. One loopful of each of the strains was inoculated into NB medium, which is a medium containing 20 g of bouillon powder, 5 g of yeast extract and 10 g of glucose in 1 liter of water and adjusted to pH 7.2, followed by shake culture at 30° C. for 16 hours for proliferation. The resulting seed cultures (0.8 ml) were inoculated into both semi-synthetic MAYE medium containing acetic acid as the carbon source [medium containing 20 g of ammonium acetate, 10 g of $(NH_4)_2SO_4$, 3 g of urea, 1 g of yeast extract, 1 g of $KH_2PO_4$, 0.4 g of $MgSO_4.7H_2O$, 2 mg of $FeSO_4.7H_2O$, 2 mg of $MnSO_4.4H_2O$, 60 μg of biotin, 2 mg of thiamine hydrochloride and 50 mg of NaCl in 1 liter of water and adjusted to pH 7.2], and MSYE medium containing sucrose as the carbon source [medium containing 20 g of sucrose, 10 g of $(NH_4)_2SO_4$, 3 g of urea, 1 g of yeast extract, 1 g of $KH_2PO_4$, 0.4 g of $MgSO_4.7H_2O$, 2 mg of $FeSO_4.7H_2O$, 2 mg of $MnSO_4.4H_2O$, 60 μg of biotin, 2 mg of thiamine hydrochloride and 20 mg of NaCl in 1 liter of water and adjusted to pH 7.2], followed by incubation at 30° C. for 16 hours.

The cells were collected, washed twice with 100 mM phosphate buffer (pH 7.0), and then suspended in 5 ml of the same buffer. Under ice cooling, the cell suspension was subjected to cell disruption for 15 minutes using a ultrasonic homogenizer (manufactured by TOMY Co., pencil type sonic). The homogenate was centrifuged at 4° C. for 10 minutes ($14000 \times g$) and the supernatant was recovered as the cell extract.

The ICL activity of the cell extract was determined by the method for quantitatively determining glyoxylic acid formed using isocitric acid as the substrate [J. Biochem., 64, 355 (1968)]. That is, to 2.0 ml of a reaction mixture [0.14M Tris-HCl (pH 7.5), 20 mM $MgSO_4.7H_2O$ and 20 mM glutathione] previously warmed to 30° C., were added the cell extract in an amount corresponding to 30 μg when calculated as protein and 20 μl of 0.4M isocitric acid solution. The reaction was carried out at 30° C. for 10 minutes and terminated by adding 1 ml of 0.5M oxalate solution to the reaction mixture. Following addition of 0.5 ml of 1% phenylhydrazine solution, the reaction mixture was heated at 70° C. for 10 minutes, followed by cooling in ice water for 5 minutes. Then, 2 ml of conc. hydrochloric acid and 0.5 ml of 0.5% potassium ferricyanide solution were added to develop a color and the absorbance was measured at 520 nm using a Hitachi Colorimeter (Model 100-20). The specific enzymatic activity per mg of protein was calculated and indicated as unit (U)/mg protein, one unit being defined as that enzymatic activity which catalyzes the formation of 1 μmol of glyoxylic acid in one minute. The results are shown in Table 1. The amount of protein was determined using a Protein Assay Kit (manufactured by BIO-RAD Co.).

In all the strains, the ICL activity was only slightly detected or not detected in the cells cultured in MSYE medium, whereas the ICL activity at high levels was noted in the cells cultured in MAYE medium. When the strains were cultured in media containing, as carbon sources, sugars such as glucose, maltose and gluconic acid, the ICL activity was very slight or not detected as in the case of the sucrose-containing medium. When the strains were cultured in media containing, as carbon sources, non-sugars such as lactic acid, ethanol and pyruvic acid, the ICL activity at the same level as in the case of the acetic acid-containing medium was detected.

The foregoing results confirmed that the expression of the ICL gene of all the coryneform bacteria used in the test was repressed when the strains were cultured in a medium containing sugars as carbon sources, and the expression was induced when the strains were cultured in a medium containing a non-sugar as carbon sources.

The cell extracts described above were analyzed by SDS-polyacrylamide gel electrophoresis (SDS-PAGE) according to the method of Laemli, Nature, 227, 680 (1970). The cell extract containing 15 μg of protein was put on 10% acrylamide gel. After electrophoresis, the gel was stained with a staining solution (0.1% Coumassie Blue R250, 50% methanol) and then decolored with a decoloring solution (40% methanol, 10% acetic acid).

By observation of the stained protein, it was confirmed with all the coryneform bacteria described above except *Corynebacterium callunae* ATCC 15991, that ICL protein having a size of about 48 kilodalton (kDa) was present in marked quantities in the cells cultured in MAYE medium. In the case of *Corynebacterium callunae* ATCC 15991, marked amounts of ICL protein was also noted only in the cells cultured in MAYE medium, but the size of the protein was about 52 kDa. In both of the strains, however, the ICL protein of 48 kDa or 52 kDa was barely or not detectable in the cells cultured in MSYE medium.

In order to determine the proportion of the formed ICL protein of 48 kDa or 52 kDa to the total cell protein, the stained gel was scanned in one direction using a one-dimensional densitometer (manufactured by Shimadzu Seisakusho Co., Model UV 265) and the distribution of color density was measured in terms of visible absorption (560 nm). The results revealed that the ICL protein of 48 kDa or 52 kDa amounted to the quantity corresponding to 5 to 10% of the total cell protein in the cells cultured in MAYE medium. The presence of these proteins was hardly detected in the cells cultured in MSYE medium.

In addition, the aforesaid cell extracts were analyzed by the Western blotting method of Towbin, H., Proc. Natl. Acad. Sci. U.S.A., 76, 4350 (1979) using an antibody to ICL protein of *Corynebacterium glutamicum* ATCC 13032. Each of cell extract of the various coryneform bacteria prepared above was put on SDS-polyacrylamide gel. After electrophoresis, a membrane filter (manufactured by ATO Co., Clear Blotting P Membrane) soaked in blotting buffer [25 mM Tris-HCl, 192 mM glycine (pH 8.3)] was put on the gel. The filter was then inserted between filter papers (manufactured by Watman Co., 3 MM) soaked in the same blotting buffer and applied to a transcription device (manufactured by ATO Co.), followed by transcription at a constant current of 180 mA for one hour. After transcription, the filter was immersed in TBS buffer solution [20 mM Tris-HCl, 0.5M NaCl (pH 7.5)] containing 1% BSA (bovine serum albumin) and allowed to stand at room temperature for one hour.

*Corynebacterium glutamicum* ATCC 13032 also was grown in MAYE medium and the extract of the obtained cells was put on SDS-polyacrylamide gel. After electrophoresis, the band corresponding to the 48 kDa protein was cut out of the gel and suspended in TBS buffer solution containing 0.05% Tween 20. The supernatant of the suspension was taken in portions and injected into a mouse to prepare a polyclonal antibody (antibody to the 48 kDa protein).

The filter subjected to transcription as described above was immersed in TBS buffer solution containing the 48 kDa protein antibody and 1% BSA, and allowed to stand at 4° C. overnight. Then, the filter was washed three times with TBS buffer solution containing 0.05% Tween 20 and immersed in TBS buffer solution containing anti-mouse IgG-peroxidase (manufactured by DACO Co.) and 1% BSA with shaking at room temperature. After one hour, the filter was washed with TBS buffer solution containing 0.05% Tween 20. The filter was then immersed in a mixture of a solution of 60 mg of 4-chloro-1-naphthol (manufactured by BIO-RAD Co.) in 20 ml of methanol and 100 ml of TBS buffer solution containing 60 µl of hydrogen peroxide to effect a color-developing reaction. The 48 kDa protein antibody reacted not only with the ICL protein of 48 kDa from *Corynebacterium glutamicum* ATCC 13032 but also with the ICL protein of 48 kDa from *Corynebacterium acetoacidophilum* ATCC 13870, *Corynebacterium herculis* ATCC 13868, *Corynebacterium lilium* ATCC 15990, *Brevibacterium immariophilum* ATCC 14068, *Brevibacterium divaricatum* ATCC 14020, *Brevibacterium flavum* ATCC 14067, *Brevibacterium lactofermentum* ATCC 13655 and *Microbacterium ammoniaphilum* ATCC 15354, and with the ICL protein of 52 kDa from *Corynebacterium callunae* ATCC 15991. From the foregoing, it was concluded that these proteins were identical or extremely similar to each other.

EXAMPLE 2

Cloning of ICL Gene of *Corynebacterium glutamicum* ATCC 13032

(1) Determination of N-terminal amino acid sequence of ICL protein

Proteins other than the ICL protein are hardly detected at about 48 kDa in the cell extract of *Corynebacterium glutamicum* ATCC 13032. The ICL protein of 48 kDa was isolated by SDS-PAGE, and the N-terminal amino acid sequence was determined.

In a manner similar to Example 1, the cell extract of *Corynebacterium glutamicum* ATCC 13032 cultured in MAYE medium was prepared and 3 µl of the extract was subjected to SDS-PAGE. After electrophoresis, the gel was immersed in a buffer for transcription [10 mM 3-cyclohexylamino-1-propanesulfonic acid, 10% methanol (pH 11.0)] at room temperature for 5 minutes. The protein on the gel was transcribed onto PVDF membrane (manufactured by Millipore Co., 0.45 µm in pore size) soaked in methanol according to the method of Towbin et al., Proc. Natl. Acad. Sci. U.S.A., 76, 4530 (1979). After being washed with deionized water for 5 minutes, the PVDF membrane was stained with Coumassie staining solution (0.1% Coumassie Blue R250, 50% methanol) for 5 minutes and then immersed in a decoloring solution (40% methanol, 10% acetic acid) for 5 minutes for decoloration. The PVDF membrane was then immersed in deionized water for 5 minutes for washing followed by air-drying. The ICL protein of 48 kDa stained on the membrane was cut out and the N-terminal amino acid sequence was determined according to the method of Matsudaira et al., J. Biol. Chem., 262, 10035 (1987).

That is, the ICL protein transcribed on the membrane was subjected to Edman degradation using a protein sequencer (manufactured by Applied Biosystems Co., Model 470) to analyze the N-terminal amino acid sequence of the protein. The amino acid sequence was determined to be as shown by Seq. ID NO:1.

(2) Synthesis of oligonucleotide probe

An oligonucleotide having the nucleotide sequence (Seq. ID NO:2) corresponding to the amino acid sequence determined as above was synthesized by the phosphoramidite method [M. H. Caruther et al., Chemical Synthesis of Gene Fragments, a Laboratory Manual, Verlag Chemie (1982)] using an oligonucleotide synthesizer (manufactured by Applied Biosystems Co., Model 380A).

This 50-mer oligonucleotide probe was 5'-labeled using $[\gamma^{32}]$ ATP (Amersham 3000 Ci/mmol) in the following manner. To 15 µl of kinase buffer solution [50 mM Tris-HCl, 10 mM MgCl$_2$, 5 mM DTT, 0.1 mM EDTA (pH 7.6)] were added 0.2 µg of the probe DNA and $[\gamma^{32}]$ ATP (150 µCi). Then, 10 units of T4 polynucleotide kinase (manufactured by Takara Shuzo Co., Ltd.) was added to the mixture and the reaction was carried out at 37° C. for 30 minutes. After phenol extraction, the reaction mixture was subjected to gel filtration using Sephadex G50 to obtain the 5'-labeled probe.

(3) Cloning of ICL gene-carrying fragment by colony hybridization

The seed culture (0.8 ml) of *Corynebacterium glutamicum* ATCC 13032 cultured in NB medium was inoculated into 40 ml of SSM medium containing 20 g of glucose, 10 g of (NH$_4$)$_2$SO$_4$, 3 g of urea, 1 g of yeast extract, 1 g of KH$_2$PO$_4$, 0.4 g of MgSO$_4$.7H$_2$O, 2 mg of FeSO$_4$.7H$_2$O, 2 mg of MnSO$_4$.4H$_2$O, 60 µg of biotin, 2 mg of thiamine hydrochloride and 50 mg of NaCl in 1 liter of water and adjusted to pH 7.2, followed by shake culture at 30° C. The optical density (OD) was measured at 660 nm with a Hitachi Colorimeter (Model 100-20), and when the OD reached 0.2, penicillin G was added to the culture at a concentration of 0.5 unit/ml. Culturing was continued until the OD reached 0.6. Then, the cells were collected from the culture, washed with TES buffer solution [0.03M Tris-HCl, 0.005M EDTA, 0.05M NaCl (pH 8.0)], and suspended in 10 ml of lysozyme solution [25% sucrose, 0.1M NaCl, 0.05M Tris-HCl, 0.8 mg/ml lysozyme (pH 8.0)]. The suspension was kept at 37° C. for 2 hours. From the collected cells, a high molecular weight chromosomal DNA was isolated according to the method of Saito et al., Biochem. Biophys. Acta, 72, 619 (1963). On the other hand, pUC19 was prepared from *E. coli* ATCC 33694 carrying pUC19 (manufactured by Takara Shuzo Co., Ltd.) in a conventional manner according to the method of Birnboim et al., Nucleic Acids Res., 7, 1513 (1979).

Twenty units of Hind III was added to 98 μl of buffer solution B [10 mM Tris-HCl (pH 7.5), 50 mM NaCl, 10 mM $MgCl_2$, 1 mM DTT] containing 5 μg of the chromosomal DNA obtained from *Corynebacterium glutamicum* ATCC 13032. The reaction was carried out at 37° C. for 2 hours. On the other hand, 5 units of Hind III was added to 48.5 μl of buffer solution B containing 1 μg of pUC19 plasmid DNA and the reaction was carried out at 37° C. for one hour. After these reaction products were mixed, phenol extraction and ethanol precipitation were carried out to recover DNAs. All of the recovered DNA was dissolved in 59 μl of ligation buffer solution [20 mM Tris-HCl (pH 7.6), 10 mM $MgCl_2$, 10 mM DTT, 1 mM ATP], and 350 units of T4 ligase was added to the solution. The ligation reaction was carried out at 16° C. for 15 hours.

*E. coli* ATCC 33694 was transformed using this DNA reaction mixture by the method of Dagert et al., Gene, 6, 23 (1979). An LB plate [1% trypton, 0.5% yeast extract, 0.5% NaCl (pH 7.4)] containing 100 μg/ml ampicillin was covered with a nitrocellulose filter (manufactured by Gelman Science Co., Bio Trace ™ NT) and the transformants were applied to the surface of the filter. After the plate was allowed to stand at 37° C. for 16 hours, colonies formed on the filter were replicated on two nitrocellulose filters. The three filters were transferred to an LB plate containing 100 μg/ml ampicillin and allowed to stand at 37° C. for 6 hours for proliferation. Two of the replicated nitrocellulose filters were transferred to an LB plate containing 250 μg/ml chloramphenicol and 100 μg/ml ampicillin. After culturing at 37° C. for 16 hours, the filters were transferred successively onto Watman 3 MM filter paper respectively soaked in 0.5M NaOH solution, 1.0M Tris-HCl (pH 7.5), 1.5M NaCl-0.5M Tris-HCl (pH 7.5) solution and 2×SSC solution [0.3M NaCl, 0.03M $Na_3$-citrate (pH 7.0)] to expose and denature the DNAs from the colonies. After air-drying, DNAs were immobilized on the filters by heating at 80° C. for 3 hours. On the other hand, the third filter was kept on the plate and stored at 4° C.

The replica filter on which the gene library had been immobilized was immersed in 3×SSC solution [0.45M NaCl, 0.045M $Na_3$-citrate (pH 7.0)] at 65° C. for 30 minutes. Then, the filter was transferred into 1×Denhardt solution (0.2% Ficoll, 0.2% polyvinylpyrrolidone, 0.2% BSA) and allowed to stand at 65° C. for one hour. The filter was put in a polypropylene bag charged with pre-hybridization buffer solution [1×Denhardt solution, 1M NaCl, 50 mM Tris-HCl (pH 8.0), 10 mM EDTA, 0.1% SDS, 100 μg/ml denatured salmon sperm DNA] and pretreated at 65° C. for 3 hours. Then, 0.2 μg of the radio isotope-labeled 50-mer oligonucleotide probe of Example 2(2) was added and hybridization was carried out at 40° C. for 16 hours. The filters were washed successively with 6×SSC solution [0.9M NaCl, 0.09M $Na_3$-citrate (pH 7.0)] twice at 4° C. for 5 minutes, twice at 52° C. for 30 minutes and twice at 4° C. for 5 minutes. After air-drying, each filter was brought into contact with an X ray film (manufactured by Fuji Photo Film Co., Ltd.) and exposed to light.

One colony hybridized to the probe out of about 8500 clones. A colony corresponding to this hybridized colony was isolated from the stored plate and a clone of the colony was tested. As the result, it was found that the clone had a structure in which a Hind III fragment of 6.0 kb had been inserted in the Hind III site of pUC19. This plasmid was named pKT4.

EXAMPLE 3

Expression of ICL Gene in ICL Gene-Amplified Strain (1) Expression of ICL gene of *Corynebacterium glutamicum* ATCC 13032 (pKT10)

In order to confirm that the ICL gene is carried on the cloned fragment described above, pKT4 was inserted into a vector for coryneform bacteria, pCG116 (Japanese Published Unexamined Patent Application No. 265892/89). Plasmid pCG116 was isolated from the cultured cells of *Corynebacterium glutamicum* ATCC 13032 carrying pCG116 according to the following method. The seed culture (8 ml) of pCG116-carrying *Corynebacterium glutamicum* ATCC 13032 grown in NB medium containing 100 μg/ml spectinomycin was inoculated into 400 ml of SSM medium containing 100 μg/ml spectinomycin, followed by shake culture at 30° C. When the OD reached 0.2, penicillin G was added to the culture at a concentration of 0.5 unit/ml. Culturing was continued until the OD reached 0.6, and then the cells were collected from the culture. After washing with TES buffer solution, the cells were suspended in 10 ml of lysozyme solution and subjected to reaction at 37° C. for 4 hours. To the reaction mixture were successively added 2.4 ml of 5M NaCl, 0.6 ml of 0.5M EDTA (pH 8.5), and 4.4 ml of a solution comprising 4% sodium lauryl sulfate and 0.7M NaCl. After gentle mixing, the mixture was allowed to stand on ice water for 15 minutes. The resulting lysate was transferred to a centrifuge tube and centrifuged at 4° C. for 60 minutes at 69,400×g to recover the supernatant. To the supernatant was added polyethylene glycol (PEG 6000) in an amount corresponding to 10% by weight, followed by gentle mixing. The resulting solution was put on ice water, and after 10 hours, it was centrifuged for 10 minutes at 1,500×g to recover pellets. TES buffer solution (5 ml) was added to dissolve the pellets, followed by addition of 2.0 ml of 1.5 mg/ml ethidium bromide. Then, 7.5 g of cesium chloride was added thereto and gently dissolved, and the density was adjusted to 1580. The resulting solution was ultra-centrifuged at 18° C. for 48 hours at 105,000×g. A high density band located at the lower part of the centrifuge tube, which was detected under UV irradiation, was taken with a syringe from the side of the centrifuge tube, thereby isolating pCG116 plasmid DNA. The fraction was treated five times with an equal amount of isopropyl alcohol solution (by volume, 90% isopropyl alcohol, 10% TES buffer solution) to extract and remove ethidium bromide. Thereafter, dialysis was carried out against TES buffer solution.

Figure 2:
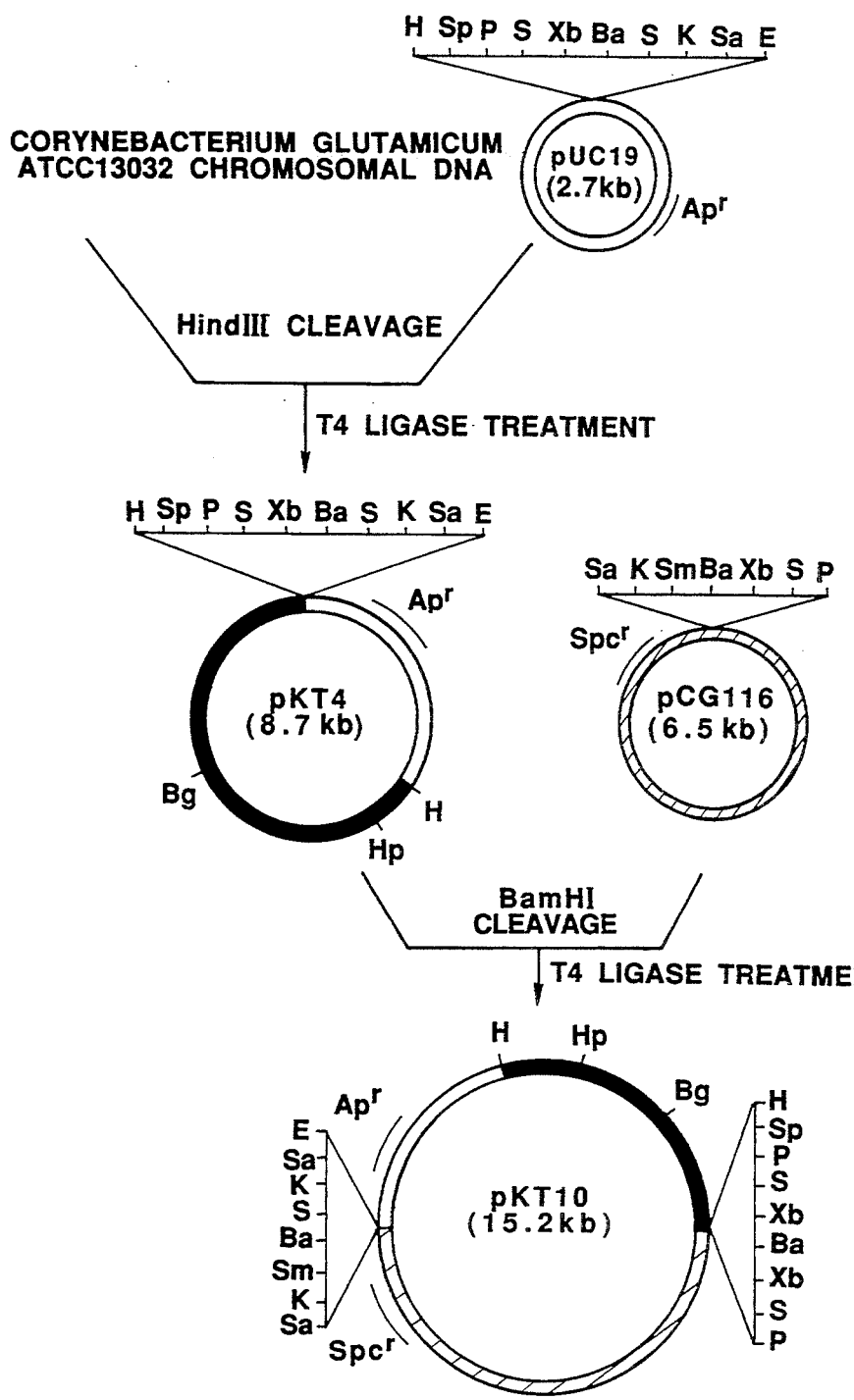
FIG. 2 shows the steps for preparing pKT10.

Five units of Bam HI was added to 19 μl of buffer solution C [10 mM Tris-HCl (pH 7.5), 100 mM NaCl, 10 mM $MgCl_2$, 1 mM DTT] containing 1 μg of pCG116 plasmid DNA, and the reaction was carried out at 37° C. for one hour. On the other hand, 5 units of Bam HI was added to 49 μl of buffer solution C containing 1 μg of pKT4 plasmid DNA isolated from the cultured cells of E. coli ATCC 33694 transformants by the process used in Example 2(3), and the reaction was carried out at 37° C. for one hour. Both reaction mixtures were subjected to 0.8% agarose gel electrophoresis, and a fragment of 6.5 kb and a fragment of 8.7 kb were respectively recovered using a kit for recovery and purification of DNA (manufactured by Asahi Glass Co., Ltd.). The DNA fragments were ligated with each other by conventional ligase treatment. E. coli ATCC 33694 was transformed using this ligase reaction mixture according to the method described in Example 2(3), and spectinomycin-resistant transformants were isolated on an LB plate containing 25 μg of spectinomycin. Plasmid pKT10 shown in FIG. 2 was isolated from one of the transformants.

pKT10 DNA (1 μg) was used for protoplast transformation of Corynebacterium glutamicum ATCC 13032 [J. Bacteriol., 159, 306 (1984)]. The protoplasts were prepared in the following manner. A seed culture (0.8 ml) of ATCC 13032 strain grown in NB medium was inoculated into 40 ml of SSM medium, followed by shake culture. When the OD reached 0.2, penicillin G was added to the culture at a concentration of 0.5 unit/ml. Culturing was continued until the OD reached 0.6. Then, the cells were collected from the culture and suspended in 10 ml of RCGP medium [medium containing 5 g of glucose, 5 g of Casamino acid, 2.5 g of yeast extract, 3.5 g of $K_2HPO_4$, 1.5 g of $KH_2PO_4$, 0.41 g of $MgCl_2.6H_2O$, 10 mg of $FeSO_4.7H_2O$, 2 mg of $MnSO_4.4-6H_2O$, 0.9 mg of $ZnSO_4.7H_2O$, 0.04 mg of $(NH_4)_6Mn_7O_{24}.4H_2O$, 30 μg of biotin, 2 mg of thiamine hydrochloride, 135 g of sodium succinate and 30 g of polyvinylpyrrolidone (molecular weight; 10000) in 1 liter of water and adjusted to pH 7.4] containing 1 mg/ml lysozyme and adjusted to pH 7.6. The suspension was allowed to stand at 30° C. for 16 hours to obtain a protoplast suspension. The protoplast suspension was centrifuged at 2,500×g for 5 minutes and the precipitated protoplasts were suspended in 1 ml of TSMC buffer solution [10 mM $MgCl_2$, 30 mM $CaCl_2$, 50 mM Tris-HCl, 400 mM sucrose (pH 7.5)], followed by centrifugation and washing. The resulting protoplasts were resuspended in 0.1 ml of TSMC buffer solution, and the suspension was mixed with 10 μl of a solution containing pKT10 plasmid DNA prepared above, followed by addition of 0.8 ml of TSMC buffer solution containing 20% PEG6000. The resulting mixture was allowed to stand in ice water for 20 minutes and then at 37° C. for 3 minutes and centrifuged at 2,500×g for 5 minutes to remove the supernatant. The precipitated protoplasts were suspended in 1 ml of RCGP medium, and 0.2 ml of the suspension was smeared on RCGP plate containing 400 μg/ml spectinomycin. Incubation was carried out at 30° C. for 7 days to obtain transformants. The plasmid contained in the transformants was analyzed by digestion with restriction enzymes, whereby it was confirmed that the transformants carried pKT10.

In a similar manner, an ICL-deficient mutant acquired as an acetic acid-non-assimilative mutant from Corynebacterium glutamicum ATCC 13032 according to a known process [J. Appl. Microbiol., 15, 27 (1969)] was transformed using pKT10 plasmid DNA solution. The ICL-deficient mutant carrying pKT10 introduced by the transformation acquired the ability of growth in MA medium containing acetic acid as a carbon source [medium containing 20 g of ammonium acetate, 10 g of $(NH_4)_2SO_4$, 3 g of urea, 1 g of $KH_2PO_4$, 0.4 g of $MgSO_4.7H_2O$, 2 mg of $FeSO_4.7H_2O$, 2 mg of $MnSO_4.4$-$H_2O$, 60 μg of biotin, 2 mg of thiamine hydrochloride and 50 mg of NaCl in 1 liter of water and adjusted to pH 7.2] and had ICL activity comparable to ATCC 13032 (pKT10) strain. It was confirmed therefrom that the Hind III DNA fragment of 6.0 kb obtained from Corynebacterium glutamicum ATCC 13032 which was present on pKT10 contained the ICL gene.

Corynebacterium glutamicum ATCC 13032 and ATCC 13032 (pKT10) were cultured at 30° C. for 16 hours in MSYE medium containing sucrose as a carbon source and in MAYE medium containing acetic acid as a carbon source. After the cells were collected, the cell extract was prepared.

The ICL activity of the cell extract was determined by the method described in Example 1. The results are shown in Table 1. The cells of ATCC 13032 (pKT10) cultured in MAYE medium showed a high level of ICL activity, as was also the case with ATCC 13032. However, the activity level of ATCC 13032 (pKT10) was about six times higher than that of ATCC 13032.

The cell extracts of the two strains were analyzed by SDS-polyacrylamide gel electrophoresis, whereby large quantities of the ICL protein of 48 kDa were detected only in the cells cultured in MAYE medium. The amount of the ICL protein of 48 kDa produced by Corynebacterium glutamicum ATCC 13032 (pKT10) was about 33% of the total cell protein, which was 5 to 6 times larger than that of ATCC 13032 strain. The foregoing results reveal that the expression of ICL gene was regulated also when the copy number was increased.

(2) Expression of amplified ICL gene in other hosts pKT10 was introduced into 9 strains of coryneform bacteria shown in Table 1 in a similar manner as in Example 3(1). Additionally, pKT10 was introduced into Brevibacterium ammoniagenes ATCC 6872 by the method described in Japanese Published Unexamined Patent Application No. 185372/88. That is, 0.8 ml of the seed culture of this strain cultured in NB medium was inoculated into 40 ml of GIII medium containing 15 g of glucose, 8 g of $(NH_4)_2SO_4$, 1.2 g of urea, 1.2 g of yeast extract, 0.5 g of $KH_2PO_4$, 0.5 g of $K_2HPO_4$, 0.1 g of $MgSO_4.7H_2O$, 2 mg of $FeSO_4.7H_2O$, 1 mg of $ZnSO_4.7H_2O$, 1 mg of $MnSO_4.4$-$6H_2O$, 0.1 mg of biotin, 2 mg of thiamine hydrochloride, 10 mg of calcium panthothenate, 100 mg of adenine and 100 mg of guanine in 1 liter of water and adjusted to pH 7.2, followed by shake culture at 30° C. Penicillin G was added to the culture at a concentration of 0.3 unit/ml at the initial stage of logarithmic growth phase (cell concentration: $10^8$ cells/ml). Culturing was continued for an additional 3 hours, and then the culture was centrifuged at 3,000 rpm for 10 minutes to recover the cells. After washing with GIII medium, the cells were suspended in 10 ml of P3 hypertonic solution [70 mM NaCl, 5 mM $MgCl_2$, 5 mM $CaCl_2$, 25 mM Tris-HCl, 1.6M D-sorbitol (pH 7 6)] containing 2.0 mg/ml lysozyme and 0.6 mg/ml achromopeptidase. The suspension was allowed to stand at 30° C. for 16 hours to prepare protoplasts. Transformants were obtained using the thus prepared protoplasts according to the method of Example 3(1).

The obtained transformants, except those of Brevibacterium ammoniagenes ATCC 6872, were cultured in MSYE medium and MAYE medium and the ICL activity of the cell extracts was determined. The ICL activity of Brevibacterium ammoniagenes ATCC 6872 and ATCC 6872 (pKT10) was determined using the cell extract of the cells cultured in MSYE medium and the cell extract of the cells obtained by culturing the cells in MSYE medium, suspending the cultured cells in MAYE medium and then incubating the suspension at 30° C. for 16 hours. As shown in Table 1, ICL activity at high levels was detected in the cells cultured in MAYE medium with all of the pKT10 transformants, as in the case of *Corynebacterium glutamicum* ATCC 13032 (pKT10).

TABLE 1

| Strain | ICL Specific Activity (U/mg protein) | |
|---|---|---|
| | MSYE Medium | MAYE Medium |
| *Corynebacterium glutamicum* | | |
| ATCC 13032 | ND | 760 |
| ATCC 13032 (pKT10) | ND | 4670 |
| *Corynebacterium acetoacidophilum* | | |
| ATCC 13870 | ND | 980 |
| ATCC 13870 (pKT10) | 170 | 6050 |
| *Corynebacterium callunae* | | |
| ATCC 15991 | ND | 480 |
| ATCC 15991 (pKT10) | ND | 4330 |
| *Corynebacterium herculis* | | |
| ATCC 13868 | ND | 350 |
| ATCC 13868 (pKT10) | 160 | 1830 |
| *Corynebacterium lilium* | | |
| ATCC 15990 | ND | 300 |
| ATCC 15990 (pKT10) | 170 | 2140 |
| *Brevibacterium immariophilum* | | |
| ATCC 14068 | ND | 130 |
| ATCC 14068 (pKT10) | 190 | 6690 |
| *Brevibacterium divaricatum* | | |
| ATCC 14020 | ND | 430 |
| ATCC 14020 (pKT10) | 140 | 3980 |
| *Brevibacterium flavum* | | |
| ATCC 14067 | ND | 550 |
| ATCC 14067 (pKT10) | 120 | 2940 |
| *Brevibacterium lactofermentum* | | |
| ATCC 13655 | ND | 230 |
| ATCC 13655 (pKT10) | 120 | 2760 |
| *Microbacterium ammoniaphilum* | | |
| ATCC 15354 | ND | 450 |
| ATCC 15354 (pKT10) | 50 | 4000 |
| *Brevibacterium ammoniagenes* | | |
| ATCC 6872 | ND | ND |
| ATCC 6872 (pKT10) | ND | 1730 |

ND: not detected

EXAMPLE 4

Analysis of ICL Gene-Carrying Fragment (1) Restriction map of DNA fragment pKT4 plasmid DNA (1 μg) was treated with 10 to 12 units of restriction enzymes (Afl II, Alu I, Bgl II, Cla I, Hind III, Hpa I, Nco I, Nru I, Sma I, Sph I, Stu I, Xho I), alone or in combination, at 37° C. (enzymes other than Sma I) or at 30° C. (Sma I) for one hour. The reaction mixture was subjected to 0.8% agarose gel electrophoresis or 5% polyacrylamide gel electrophoresis. Measurement of the size of the fragments formed revealed that the cloned Hind III DNA fragment of 6.0 kb had a structure shown by the restriction map of FIG. 1.

(2) Subcloning

Figure 3:
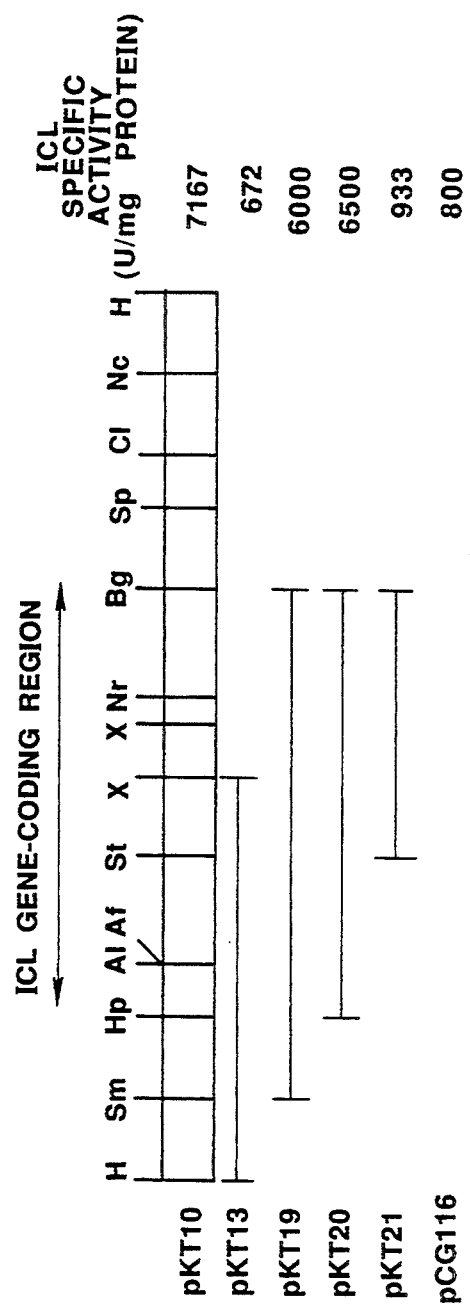
FIG. 3 is a restriction map of a cloned Hind III-cleaved DNA fragment of 6.0 kb carrying the ICL gene in subcloning.

In order to locate the ICL gene cloned on the 6.0 kb Hind III DNA fragment, several regions were subcloned. Ten units each of Hind III and Xho I were added to 48 μl of buffer solution C containing 2 μg of pKT4 plasmid, and the reaction was carried out at 37° C. for 2 hours. On the other hand, 10 units each of Hind III and Xho I were added to 18 μl of buffer solution C containing 2 μg of pUC19, and the reaction was carried out at 37° C. for 2 hours. Both reaction mixtures were subjected to 0.8% agarose gel electrophoresis, and a fragment of 1.9 kb and a fragment of 2.7 kb were respectively recovered using a kit for recovery and purification of DNA. The two DNA fragments were ligated with each other by ligase treatment in conventional manner. The ligase reaction mixture was used for transformation of *E. coli* ATCC 33694 and plasmid pKT5 was obtained. pKT5 DNA was then digested with Kpn I and ligated with pCG116 plasmid DNA, which is a vector for *Corynebacterium glutamicum*, digested with the same restriction enzyme to prepare plasmid pKT13. In addition, 2.2 kb Sma I-Bgl II fragment, 2.1 kb Hpa I-Bgl II fragment and 1.2 kb Stu I-Bgl II fragment were obtained from pKT4 and then inserted into Sma I-Bam HI linker site of pCG116 to prepare plasmids pKT19, pKT20 and pKT21, respectively. The DNA fragments cloned on these plasmids are shown in FIG. 3.

*Corynebacterium glutamicum* ATCC 13032 was transformed with these plasmid DNAs. The transformants were cultured in MAYE medium and the ICL activity of the cultured cells was determined (FIG. 3). The pKT19-carrying strain and the pKT20-carrying strain showed an activity level as high as that of the pKT10-carrying strain, whereas the pKT13-carrying strain and the pKT21-carrying strain only gave the activity at almost the same level as that of the host. On the basis of these results, the ICL gene was to be located on the 2.1 kb Hpa I-Bgl II DNA fragment shown by an arrow in the upper part of FIG. 3.

(3) Nucleotide sequence of the region of ICL gene

The Hpa I-Bgl II DNA fragment of 2.1 kb encoding ICL was digested at its restriction enzyme sites and inserted into plasmids pUC118 and pUC119 (manufactured by Takara Shuzo Co., Ltd.) digested with the corresponding restriction enzymes. By using the thus prepared plasmids, the nucleotide sequence of the fragment encoding ICL was determined according to a modification of the M13 chain termination method by Messing et al., Methods in Enzymology, 101, 20 (1983). The result is shown by the DNA nucleotide sequence and the amino acid sequence corresponding to the ICL structural gene represented by Seq. ID NO:3. The nucleotide sequence was found to contain the open reading frame (1293 bp) comprising 431 amino acid residues including the sequence corresponding to codons for 17 amino acids out of the N-terminal 18 amino acid residues shown in Example 2(1). This indicates that ICL promoter activity is attributable to the DNA sequence upstream of ATG. At the position downstream of stop codon TAG by 27 bp, a sequence considered to function in the termination of transcription was present at positions 1833 to 1846 and 1850 to 1863 of the DNA nucleotide sequence shown by Seq. ID NO:3.

EXAMPLE 5

Homology of ICL Genes of Coryneform bacteria

Homology of chromosomal DNA fragments of various coryneform bacteria was examined according to the Southern hybridization method of Read et al., Nucleic Acid Res., 13, 7207 (1985) using as a probe the 50-mer oligonucleotide corresponding to the N-terminal amino acid sequence of ICL described in Example 2(2) or an Hpa I-Afl II fragment of 0.5 kb (Seq. ID NO: 3) which is 5'-untranslated region.

In order to prepare the Hpa I-Afl II fragment of 0.5 kb, 10 units of Afl II was added to 49 μl of buffer solution E [10 mM Tris-HCl (pH 7.5), 40 mM KCl, 10 mM MgCl$_2$, 1 mM DTT] containing 2 μg of plasmid pKT10 (FIGS. 2 and 3) and the reaction was carried out at 37° C. for one hour. Then, 3 μl of 1M KCl and 10 units of Hpa I were further added to the mixture and the reaction was carried out at 37° C. for one hour. The reaction mixture was subjected to 1.2% agarose gel electrophoresis and the 0.5 kb Hpa I-Afl II fragment was recovered using a kit for recovery and purification of DNA.

The 50-mer oligonucleotide was labeled at the 5' end according to the method of Example 2(2). The 0.5 kb Hpa I-Afl II fragment was labeled with [$^{32}$P] using Nick Translation Kit (manufactured by Takara Shuzo Co., Ltd.).

Chromosomal DNAs were prepared from *Corynebacterium glutamicum* ATCC 13032, *Corynebacterium acetoacidophilum* ATCC 13870, *Corynebacterium callunae* ATCC 15991, *Corynebacterium herculis* ATCC 13868, *Brevibacterium divaricatum* ATCC 14020, *Brevibacterium lactofermentum* ATCC 13655 and *Microbacterium ammoniaphilum* ATCC 15354 respectively according to the method described in Example 2(3). To 98 μl of buffer solution B containing 5 82 g of each chromosomal DNA was added 20 units of Hind III, and the reaction was carried out at 37° C. for 2 hours. Ten microliters each of these reaction mixtures were respectively subjected to 0.8% agarose gel electrophoresis. After the electrophoresis, the gel was immersed in 0.25M HCl and shaken for 15 minutes. Then, the gel was rinsed with deionized water and put on a filter paper (Watman 3 MM) soaked in 0.4M NaCl. A nylon filter (manufactured by BIO-RAD Co., Ltd., Zeta Probe Membrane), a filter paper and an appropriate weight were successively layered on the gel and 0.4M NaOH was provided from the back of the gel through the filter paper to transfer DNA onto the nylon filter. The filter was washed with 6×SSC, air-dried and subjected to a hybridization test. The filter was immersed in 20 ml of a prehybridization solution (6× SSC, 0.01M EDTA, 1% Ficoll, 1% polyvinylpyrrolidone, 1% bovine serum albumin, 0.5% SDS, 0.1 mg/ml denatured salmon sperm DNA) and heated at 68° C. for 3 hours. Then, the filter was transferred to a hybridization solution obtained by adding 0.2 μg of each labeled probe to 20 ml of the prehybridization solution. When the 50-mer oligonucleotide was used as a probe, hybridization was carried out at 40° C. for 16 hours. In the case of the 0.5 kb Hpa I-Afl II fragment, hybridization was carried out at 68° C. for 16 hours. The treated filter was then immersed in SWS (0.3×SSC, 0.05% SDS). When the 50-mer oligonucleotide was used as a probe, treatment at 52° C. for 30 minutes was carried out twice; and when the 0.5 kb Hpa I-Afl II fragment was used as a probe, treatment at 68° C. for 30 minutes was carried out twice. After washing, each filter was air-dried, brought into contact with an X ray film (manufactured by Fuji Photo Film Co., Ltd.) and exposed to light.

In the case of the coryneform bacteria other than *Corynebacterium callunae* ATCC 15991, hybrids with Hind III chromosomal DNA fragments of about 6.0 kb were formed by using either probe. On the other hand, in the case of *Corynebacterium callunae* ATCC 15991, hybrids with Hind III chromosomal DNA fragments of about 2.0 kb were formed by using either probe. These results reveal that the ICL genes of coryneform bacteria have homology to that of *Corynebacterium glutamicum* ATCC 13032 not only in the ICL structural gene region but also in the promoter region.

EXAMPLE 6

Figure 4:
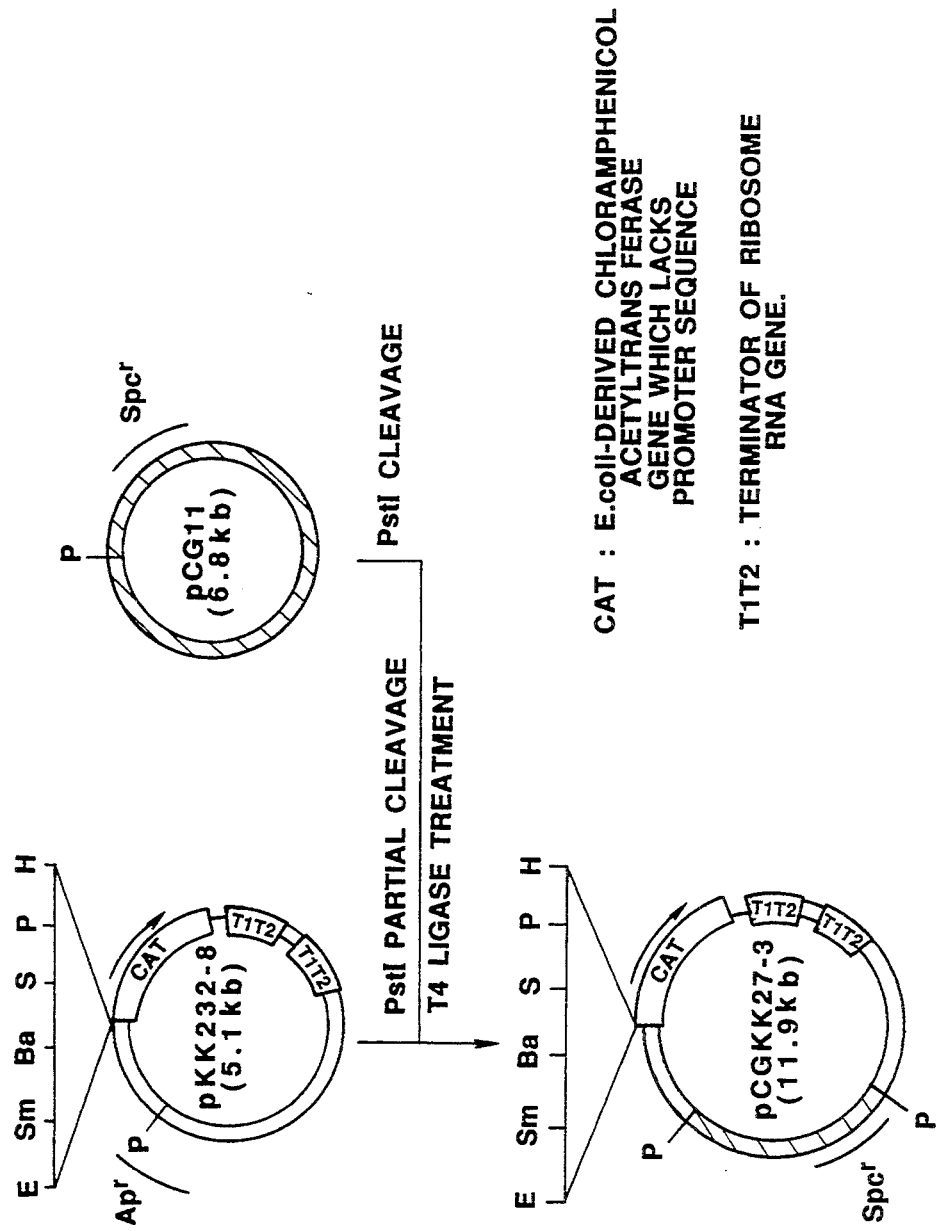
FIG. 4 shows the steps for preparing pCGKK27-3.

Expression of Chloramphenicol Acetyltransferase Structural Gene by the ICL Promoter Plasmid pKK232-8 of *E. coli* carries a DNA fragment which contains in its structure: (1) the region from the sequence necessary for translation initiation to the structural gene in the *E. coli*-derived chloramphenicol acetyltransferase gene region lacking the promoter sequence; and (2) located downstream of the region, terminator T$_1$T$_2$ derived from *E. coli* ribosome RNA gene [Brosius, J., Gene, 27, 151 (1984)]. Plasmid pCGKK27-3 containing the DNA fragment and capable of replicating in coryneform bacteria was prepared as shown in FIG. 4.

To 50 μl of buffer solution C containing 5 μg of pKK232-8 (manufactured by Pharmacia Fine Chemicals) was added 0.3 unit of Pst I. After treatment at 37° C. for one hour, the mixture was heated at 68° C. for 10 minutes to terminate the reaction. On the other hand, 2 μg of pCG11, a vector for coryneform bacteria (Japanese Published Unexamined Patent Application No. 134500/82), prepared from a pCG11-carrying strain by the method described in Japanese Published Unexamined Patent Application No. 186489/82 was treated with 12 units of Pst I in 49 μl of buffer solution C at 37° C. for one hour, followed by heating. The reaction mixtures of pKK232-8 and pCG11 were subjected to 0.8% agarose gel electrophoresis, and a DNA fragment of 5.1 kb and a DNA fragment of 6.8 kb were respectively recovered using a kit for recovery and purification of DNA. The DNA fragments were mixed with each other and T4 ligase was added to the mixture to cause ligation.

*E. coli* ATCC 33694 was transformed using this ligase reaction mixture according to the method described in Example 2(3), and spectinomycin-resistant transformants were isolated on an LB plate containing 25 μg/ml spectinomycin. Plasmid DNAs extracted from the transformants were analyzed by digestion with restriction enzymes. From one of the transformants, plasmid pCGKK27-3 carrying pKK232-8 ligated with pCG11 was obtained as shown in FIG. 4.

*Corynebacterium glutamicum* ATCC 13032 was transformed with pCGKK27-3 by the method described in Example 3(1). It was confirmed that the transformant selected on the basis of spectinomycin resistance carried pCGKK27-3 but did not show chloramphenicol resistance and the chloramphenicol acetyltransferase structural gene was not expressed in ATCC 13032.

A DNA fragment having ICL promoter activity was inserted into pCGKK27-3 (cf. FIG. 5). As the fragment containing the ICL promoter, the Sma I-Alu I fragment of 0.6 kb shown in FIG. 3 was used. pKT19 (5 μg) was treated with 10 units of Sma I in 49 μl of buffer solution D [10 mM Tris-HCl (pH 7.5), 20 mM KCl, 10 mM MgCl$_2$, 1 mM DTT] at 30° C. for one hour. Then, 6 μl of 0.2M KCl and 10 units of All II were added to the reaction mixture followed by reaction at 37° C. for one hour. The reaction mixture was subjected to 1% agarose gel electrophoresis, and a Sma I-All II DNA fragment of 0.8 kb was isolated using a kit for recovery and purification of DNA. To 49 μl of buffer solution A [10 mM Tris-HCl (pH 7.5), 10 mM MgCl$_2$, 1 mM DTT] containing this DNA was added 10 units of Alu I. The reaction was carried out at 37° C. for one hour, followed by heating at 68° C. for 10 minutes to prepare a solution containing the Sma I-Alu I DNA fragment.

On the other hand, 5 μg of pCGKK27-3 isolated from the transformant of *Corynebacterium glutamicum* ATCC 13032 was treated with 10 units of Sma I in 49 μl of buffer solution D at 30° C. for one hour, followed by heat treatment.

The obtained solution containing pCGKK27-3 was mixed with the aforesaid solution containing Sma I-Alu I DNA fragment, followed by treatment with ligase in conventional manner. *Corynebacterium glutamicum* ATCC 3032 was transformed with this ligase reaction mixture, and the cell suspension was smeared on RCGP plate containing 10 mg/ml ammonium acetate, 400 μg/ml spectinomycin and 5 μg/ml chloramphenicol. Incubation was carried out at 30° C. for 7 days to obtain colonies of the transformants. From one of the transformants, plasmid pKT22 was obtained, which had a structure wherein the Sma I-Alu I DNA fragment was inserted just before the DNA fragment containing the chloramphenicol acetyltransferase structural gene (see FIG. 5).

This transformant and ATCC 13032 strain were each cultured in MSYE medium and MAYE medium at 30° C. for 16 hours. The cultured cells were collected and disrupted, and the obtained cell extracts were examined for chloramphenicol acetyltransferase activity by the method of Shaw et al., Methods in Enzymology, 43, 737 (1975). The activity was indicated as U/mg protein, one unit being defined as that enzymatic activity which catalyzes the acetylation of 1 μmol of chloramphenicol in one minute.

pKT22 was introduced into the coryneform bacteria shown in Table 2 in a similar manner as above. The obtained transformants were cultured in MSYE medium and MAYE medium and the chloramphenicol acetyltransferase activity of the cell extracts was determined. The results are shown in Table 2.

TABLE 2

| | Chloramphenicol Acetyltransferase Specific Activity (U/mg protein) | |
|---|---|---|
| Strain | MSYE Medium | MAYE Medium |
| *Corynebacterium glutamicum* | | |
| ATCC 13032 | 0 | 0 |
| ATCC 13032 (pKT22) | 0.6 | 27.4 |
| *Corynebacterium herculis* | | |
| ATCC 13868 | 0 | 0 |
| ATCC 13868 (pKT22) | 0.2 | 13.2 |
| *Brevibacterium divaricatum* | | |
| ATCC 14020 | 0 | 0 |
| ATCC 14020 (pKT22) | 0.5 | 25.8 |
| *Brevibacterium lactofermentum* | | |
| ATCC 13655 | 0 | 0 |
| ATCC 13655 (pKT22) | 0.3 | 22.0 |
| *Brevibacterium ammoniagenes* | | |
| ATCC 6872 | 0 | 0 |
| ATCC 6872 (pKT22) | 0.1 | 12.6 |

As shown in Table 2, the transformants produced chloramphenicol acetyltransferase in large amounts when cultured in MAYE medium. Marked amounts of chloramphenicol acetyltransferase were observed as a protein band of 24 kDa in analysis by SDS-polyacrylamide gel electrophoresis.

From the foregoing results, it was confirmed that the expression of the chloramphenicol acetyltransferase structural gene was induced by the ICL promoter.

EXAMPLE 7

Expression of β-Galactosidase Structural Gene by the ICL Promoter

Figure 6:
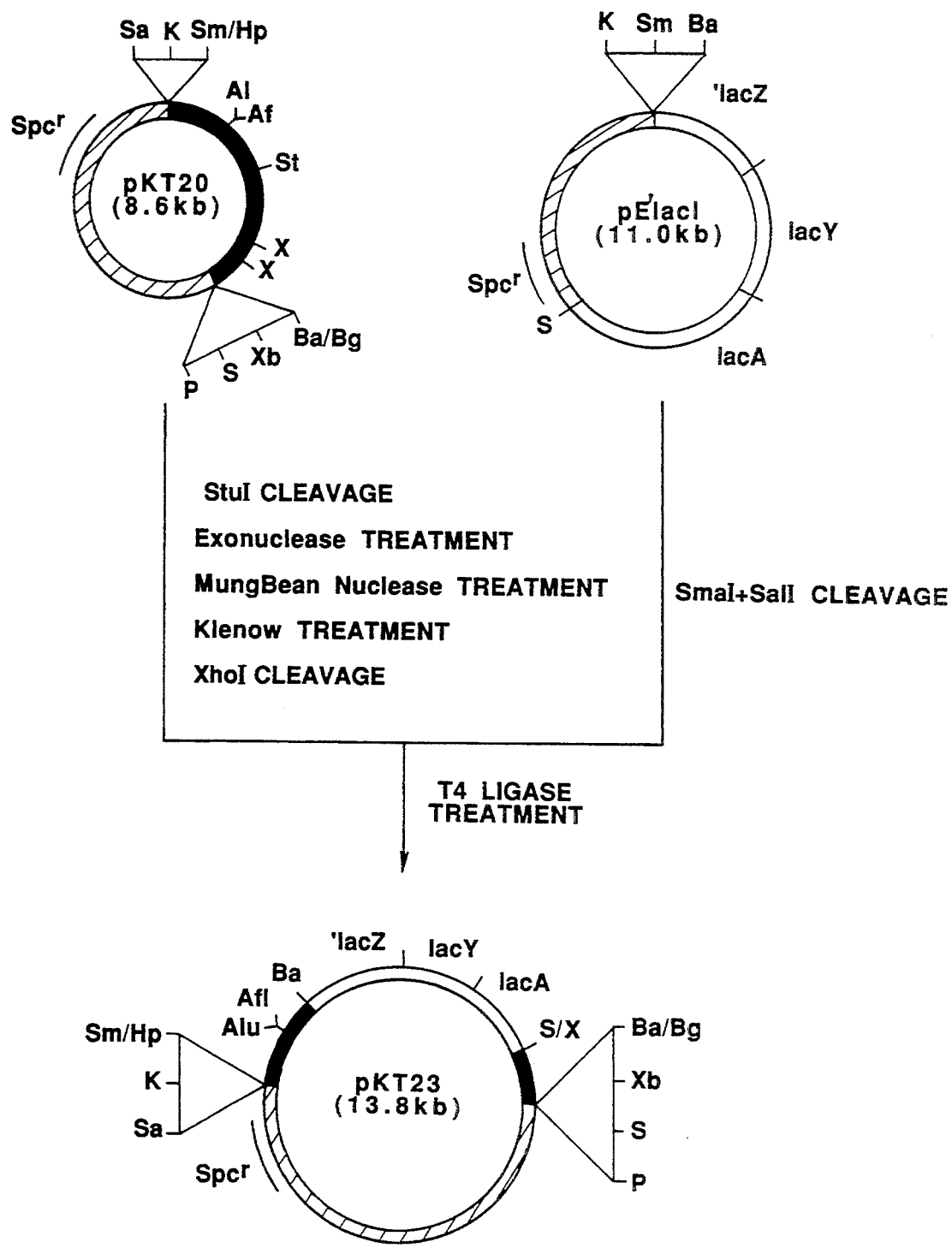
FIG. 6 shows the steps for preparing pKT23.

An expression vector capable of expressing β-galactosidase structural gene of *E. coli* by the ICL promoter was prepared according to the steps outlined in FIG. 6.

To 98 μl of buffer solution C containing 10 μg of plasmid pKT20 carrying the ICL gene was added 24 units of Stu I. After reaction at 37° C. for 2 hours, the reaction mixture was extracted once with an equal amount of phenol. Further, extraction was carried out once with an equal amount of chloroform/isoamyl alcohol (24/1, v/v), followed by ethanol precipitation and vacuum drying. The obtained DNA was subjected to a deletion treatment with exonuclease III using a Kilo Sequence Deletion Kit (manufactured by Takara Shuzo Co., Ltd.). Twenty units of Xho I was added to 40 Nl of buffer solution C containing the deletion fragments, and the reaction was carried out at 37° C. for 2 hours.

Separately, a DNA fragment containing the β-galactosidase structural gene was prepared from plasmid pE′lac1 (Japanese Published Unexamined Patent Application No. 273469/88). Plasmid pE′lac1 contains a DNA sequence wherein the region upstream of the codon for the 8th amino acid from the N-terminus of the β-galactosidase structural gene in the lactose operon of *E. coli* is deleted. To 49 μl of buffer solution D containing 5 μg of pE′lac1 was added 10 units of Sma I, and the reaction was carried out at 30° C. for 2 hours. Then, 1.5 μl of 5M NaCl and 10 units of Sal I were added to the reaction mixture, and the reaction was carried out at 37° C. for 2 hours. The digested fragments of plasmids pKT20 and pE′lac1 were separated by 0.8% agarose gel electrophoresis, and a fragment of about 7.6 kb and a fragment of about 6.2 kb were respectively recovered using a kit for recovery and purification of DNA. The fragments were ligated with each other by ligase treatment in conventional manner.

*Corynebacterium glutamicum* ATCC 13032 was transformed using this ligase reaction mixture by the method of Example 3(1). Then, the cell suspension was smeared on RCGP plate containing 400 μg/ml spectinomycin, 40 μg/ml 5-bromo-4-chloro-3-indolyl-μ-D-galactoside (X-gal) and 0.01 g/ml ammonium acetate. Incubation was carried out at 30° C. for 7 days to obtain the transformants stained blue on the plate. One of the transformants carried plasmid pKT23 in which the lactose operon-derived DNA fragment of 6.2 kb was inserted into the DNA fragment carrying the ICL gene (see FIG. 6).

This transformant and *Corynebacterium glutamicum* ATCC 13032 were cultured in MSYE medium and MAYE medium at 30° C. for 16 hours. The cultured cells were collected and disrupted, and the cell extracts were examined for β-galactosidase activity according to the method of Miller et al., Experiments in Molecular Genetics, 352, Cold Spring Harbor Laboratory (1972). The specific enzymatic activity per mg of protein was calculated and indicated as U/mg protein, one unit being defined as that enzymatic activity which catalyzes the formation of 1 μmol of o-nitrophenol in one minute.

pKT23 was introduced into the coryneform bacteria shown in Table 3 in a similar manner as above. The obtained transformants were cultured in MSYE medium and MAYE medium and the β-galactosidase activity of the cell extracts was determined. The results are shown in Table 3.

TABLE 3

| Strain | β-galactosidase Specific Activity (U/mg protein) | |
|---|---|---|
| | MSYE Medium | MAYE Medium |
| *Corynebacterium glutamicum* | | |
| ATCC 13032 | 0 | 0 |
| ATCC 13032 (pKT23) | 700 | 30900 |
| *Corynebacterium herculis* | | |
| ATCC 13868 | 0 | 0 |
| ATCC 13868 (pKT23) | 300 | 14400 |
| *Brevibacterium divaricatum* | | |
| ATCC 14020 | 0 | 0 |
| ATCC 14020 (pKT23) | 500 | 27500 |
| *Brevibacterium lactofermentum* | | |
| ATCC 13655 | 0 | 0 |
| ATCC 13655 (pKT23) | 350 | 22700 |

As shown in the table, only the transformants produced β-galactosidase in large amounts when cultured in MAYE medium. Marked amounts of β-galactosidase were detected as a protein band of a little larger than 116 kDa in the analysis by SDS-polyacrylamide gel electrophoresis.

The ligation site of the DNA fragment of the 5'-end region in the ICL gene region and the β-galactosidase structural gene on pKT23 was examined. To 49 μl of buffer solution A containing 2 μg of pKT23 and 2 μg of plasmid pUC118 (manufactured by Takara Shuzo Co., Ltd.), respectively, was added 10 units of Kpn I, and the reaction was carried out at 37° C. for 2 hours. Then, 0.5 μl of 5M NaCl and 10 units of Bam HI were added to the reaction mixture and the volume of the mixture was adjusted to 55 μl by addition of sterilized water. The reaction was carried out at 37° C. for 2 hours. These digestion products of pKT23 and pUC118 were subjected to 0.8% agarose gel electrophoresis, and a fragment of about 0.7 kb and a fragment of about 7.2 kb were respectively recovered using a kit for recovery and purification of DNA. After the fragments were ligated by ligase treatment in conventional manner, the nucleotide sequence of the obtained DNA was determined according to the method described in Example 4(3).

The result revealed that the β-galactosidase structural gene lacking N-terminal 8 amino acids was ligated in frame with the DNA fragment encoding the 1st to 63rd amino acids from the N-terminus of isocitrate lyase shown by Seq. ID NO:4.

From the foregoing results, it was confirmed that the synthesis of β-galactosidase-fused protein was induced under the control of the ICL promoter.

---

What is claimed is:

1. An isolated DNA which consists of a DNA from the isocitrate lyase gene of a coryneform bacterium, said DNA having at least a functional nucleotide sequence of nucleotide sequence 1 to 702 of SEQ ID NO:4, which regulates expression of a structural gene encoding a protein by repressing expression when carbon sources in a culture medium are sugars and inducing expression when carbon sources in a culture medium are non-sugars or a medium contains no sugar when functionally incorporated into a vector DNA together with said structural gene and introduced into a host coryneform bacterium.

2. The DNA according to claim 1, wherein said structural gene is a gene encoding an enzyme or a protein selected from the group consisting of isocitrate lyase, β-galactosidase, chloramphenicol acetyltransferase, insulin, growth hormone, interferon and granulocyte colony stimulating hormone.

3. The DNA according to claim 1, wherein said isocitrate lyase gene is obtained from a coryneform bacterium belonging to the genus Corynebacterium, Brevibacterium or Microbacterium.

4. The DNA according to claim 3, wherein said coryneform bacterium is selected from the group consisting of *Corynebacterium glutamicum* ATCC 13032, *Corynebacterium acetoacidophilum* ATCC 13870, *Corynebacterium acetoglutamicum* ATCC 15806, *Corynebacterium callunae* ATCC 15991, *Corynebacterium herculis* ATCC 13868, *Corynebacterium melassecola* ATCC 17965, *Corynebacterium lilium* ATCC 15990, *Brevibacterium immariophilum* ATCC 14068, *Brevibacterium saccharolyticum* ATCC 14066, *Brevibacterium thiogenitalis* ATCC 19240, *Brevibacterium divaricatum* ATCC 14020, *Brevibacterium flavum* ATCC 14067, *Brevibacterium*

*lactofermentum* ATCC 13869, *Brevibacterium roseum* ATCC 13825 and *Microbacterium ammoniaphilum* ATCC 15354.

5. The DNA according to claim 1, wherein said host coryneform bacterium belongs to the genus Corynebacterium, Brevibacterium or Microbacterium.

6. The DNA according to claim 5, wherein said host coryneform bacterium is selected from the group consisting of *Corynebacterium glutamicum* ATCC 13032, *Corynebacterium acetoacidophilum* ATCC 13870, *Corynebacterium acetoglutamicum* ATCC 15806, *Corynebacterium callunae* ATCC 15991, *Corynebacterium herculis* ATCC 13868, *Corynebacterium melassecola* ATCC 17965, *Corynebacterium lilium* ATCC 15990, *Brevibacterium immariophilum* ATCC 14068, *Brevibacterium saccharolyticum* ATCC 14066, *Brevibacterium thiogenitalis* ATCC 19240, *Brevibacterium divaricatum* ATCC 14020, *Brevibacterium flavum* ATCC 14067, *Brevibacterium lactofermentum* ATCC 13869, *Brevibacterium roseum* ATCC 13825, *Brevibacterium ammoniagenes* ATCC 6872 and *Microbacterium ammoniaphilum* ATCC 15354.

7. A recombinant DNA prepared by incorporating into a vector DNA (1) a DNA which consists of a DNA from the isocitrate lyase gene of a coryneform bacterium said DNA having at least a functional nucleotide sequence of nucleotide sequence 1 to 702 of SEQ ID NO: 4, which regulates expression of a structural gene encoding a protein by repressing expression when carbon sources in a culture medium are sugars and inducing expression when carbon sources in a culture medium are non-sugars or a medium contains no sugar when incorporated into said vector DNA together with said structural gene and introduced into a host coryneform bacterium and (2) a structural gene encoding a protein.

8. A coryneform bacteria transformant host carrying a recombinant DNA prepared by incorporating into a vector DNA autonomously replicable in said host (1) a DNA sequence from the isocitrate lyase gene of a coryneform bacterium, said DNA sequence having at least a functional nucleotide sequence of nucleotide sequence 1 to 702 of SEQ ID NO: 4, which regulates expression of a structural gene encoding a protein by repressing expression when carbon sources in a culture medium are sugars and inducing expression when carbon sources in a culture medium are non-sugars or a medium contains no sugar when incorporated into said vector DNA together with said structural gene and introduced into said host coryneform bacterium and (2) a structural gene encoding a protein.

* * * * *